United States Patent [19]

Wood et al.

[11] Patent Number: 5,322,692
[45] Date of Patent: Jun. 21, 1994

[54] SUSTAINED RELEASE BOLUS EFFECTIVE FOR THE PROLONGED PREVENTION, TREATMENT OR CONTROL OF NEMATODE, ACARID AND ENDO- AND ECTOPARASITIC INFESTATIONS OF RUMINANTS

[75] Inventors: Irwin B. Wood, Yardley, Pa.; Richard B. Toothill, Warren, N.J.; Joseph C. Dietz, Terre Haute, Ind.

[73] Assignee: American Cyanamid Company, Wayne, N.J.

[21] Appl. No.: 67,877

[22] Filed: May 25, 1993

Related U.S. Application Data

[60] Continuation of Ser. No. 727,734, Jul. 10, 1991, abandoned, which is a division of Ser. No. 316,625, Feb. 28, 1989, abandoned.

[51] Int. Cl.$^5$ .............................................. A61K 31/35
[52] U.S. Cl. ................................... 424/438; 424/484; 424/DIG. 10; 514/450
[58] Field of Search ................ 424/438, DIG. 10; 514/450

[56] References Cited

U.S. PATENT DOCUMENTS

| | | | |
|---|---|---|---|
| 4,166,107 | 8/1979 | Miller et al. | 424/438 |
| 4,326,522 | 4/1982 | Guerrero et al. | 128/260 |
| 4,670,248 | 6/1987 | Schricker | 424/438 |
| 4,806,527 | 2/1989 | Christenson et al. | 514/30 |
| 4,831,016 | 5/1989 | Mrozik et al. | 514/30 |
| 4,847,243 | 7/1989 | Wallace | 514/30 |
| 4,866,830 | 12/1989 | Asato et al. | 514/450 |
| 4,869,901 | 8/1989 | Wood et al. | 424/43 |
| 4,886,829 | 12/1989 | Asato et al. | 514/450 |
| 4,895,837 | 1/1990 | Mrozik et al. | 514/30 |
| 4,916,154 | 4/1990 | Asato et al. | 514/450 |

FOREIGN PATENT DOCUMENTS

| | | |
|---|---|---|
| 236901 | 9/1987 | European Pat. Off. . |
| 240274 | 10/1987 | European Pat. Off. . |
| 2166436A | 9/1985 | United Kingdom . |

*Primary Examiner*—Paul R. Michl
*Assistant Examiner*—Raj Bawa
*Attorney, Agent, or Firm*—P. A. Climenson

[57] ABSTRACT

A sustained release bolus composition, containing a prophylactically effective amount of a compound selected from LL-F28249α, 23-(O-methyloxime)-LL-F28249α and derivatives thereof provides a method for protecting ruminant animals for a prolonged period of time against infestation by nematodes, acarids and end-oand ectoparasitic insects, and which over time can also eliminate the initial population of parasites present at treatment. The invention also relates to a method for the systemic control of ectoparasitic insect infestations of ruminant animals by orally administering to said animals a sustained release bolus containing an insecticidally effective amount of LL-F28249α, 23-(O-methyloxime) LL-F-28249α or derivative thereof, which continuously releases into the rumen of the treated animal a systemically effective amount of LL-F28249α, 23-(O-methyloxime)LL-F28249α or derivative thereof.

6 Claims, No Drawings

SUSTAINED RELEASE BOLUS EFFECTIVE FOR THE PROLONGED PREVENTION, TREATMENT OR CONTROL OF NEMATODE, ACARID AND ENDO- AND ECTOPARASITIC INFESTATIONS OF RUMINANTS

This is a continuation of copending application Ser. No. 07/727,734, field on Jul. 10, 1991 now abandoned, which was a divisional of copending application, Ser. No. 07/316,625 filed on Feb. 28, 1989 now abandoned.

BACKGROUND OF THE INVENTION

The compound LL-F28249α is disclosed in the U.S. patent application of G. T. Carter et al, Ser. No. 732,252 filed May 10, 1985, now U.S. Pat. No. 5,111,038 issued on May 5, 1992 which is a Continuation-in-Part of application Ser. No. 617,650 filed Jun. 5, 1984 now U.S. Pat. No. 5,091,120, issued on Feb. 25, 1992 and incorporated herein by reference thereto. The compound LL-F28249α is produced by fermentation of the microorganism Streptomyces cyaneogriseus subspecies non-cyanogenus deposited in the NRRL under deposit accession No. 15,773. The use of LL-F28249α for the control of helminths, arthropod ectoparasites and acarids is disclosed in the U.S. patent application of I. B. Wood et al, Ser. No. 732,251 filed May 10, 1985 now U.S. Pat. No. 5,224,626 issued on Jul. 6, 1993 which is a Continuation-in-Part of application Ser. No. 617,649 filed Jun. 5, 1984 now abandoned.

The 23-(O-methyloxime) derivative of LL-F28249α is disclosed in the U.S. patent application of G. Asato et al, Ser. No. 088,953 filed Aug. 27, 1987 now U.S. Pat. No. 4,916,154 issued on Apr. 10, 1990 which is a Continuation-in-Part of application Ser. No. 06/907,283 filed Sep. 12, 1986 now abandoned and is, likewise, incorporated herein by reference thereto.

Although the inventors named in the above-identified applications have described the compounds of the present invention and have indicated that such compounds are effective for control or treatment of endo- and ecto-parasitic infections in warm-blooded animals and for the control of nematodes in soil, no entirely satisfactory method has been provided for protecting ruminant animals for a prolonged period of time, i.e. for about 3 to 6 months, by means of a single treatment.

Thus, although the inventions of G. T. Carter et al; I. B. Wood et al and G. Asato et al are effective for treating animals that can be medicated on a daily or weekly basis, satisfactory methods for the treatment of range animals and animals put out to pasture still presents a serious problem for cattlemen, sheep herders and farmers that rely on range lands to feed their ruminant livestock.

It is therefore an object of the present invention to provide a one dose treatment method for ruminant animals whereby said treated animals are protected for about 3 to 6 months against infestation by nematodes, endoparasitic insects, ectoparasitic insects acarids and ruminant pastures are protected against contamination by the infective stages of these parasites that infest said animals.

It is also an object of this invention to provide a bolus composition containing a nematicidally, insect endo- or ectoparasiticidally or acaricidially effective amount of a compound selected from LL-F28249α and 23-(O-methyloxime)LL-F28249α; said bolus being useful for the protection of ruminant animals against infestation by nematodes, endoparasitic insects, ectoparasitic insects and acarids, for prolonged periods of time.

It is a further object of this invention to provide a bolus for oral administration to ruminant animals whereby such bolus continuously releases into the rumen of said treated animals, for about 120 to 180 days, about 0.001 mg/kg/day to 0.075 mg/kg/day of LL-F28249α or 23-(O-methyloxime)LL-28249α or derivative thereof.

It is a still further object of this invention to provide a method for the systemic control of ectoparasitic insect infestations of ruminant animals by orally administering to said animals a sustained release bolus containing an insecticidally effective amount of LL-F28249e, 23-(O-methyloxine) LL-F28249α or derivative thereof, which continuously releases into the rumen of a treated animal a systemically effective amount of an insecticide selected from LL-F28249α, 23-(O-methyloxine) LL-F28249α and derivatives thereof.

SUMMARY OF THE INVENTION

This invention relates to bolus compositions containing a prophylactically effective amount of the compound LL-F28249α, 23-(O-methyloxime)LL-F28249α or derivative thereof and the administration thereof to ruminant animals to prevent or control nematode, endoparasitic insect, ectoparasitic insect or acarid infestations in said animals for a prolonged period of time.

More particularly, the present invention relates to novel sustained release boluses comprising about 0.3% to 10.04 by weight of LL-F28249α, 23-(O-methyloxime)LL-F28249α or derivative thereof, about 10.0% to 20.0% by weight of glycerol monostearate, about 3.04 to 10.0% by weight of carnauba wax and about 70.04 to 85.04 by weight of barium sulfate. It also relates to a method for protecting ruminant animals for a prolonged period of time against infestation by nematodes, endo- and ectoparasitic insects and acarids, and decontaminating pastures to eliminate the infective stages of said parasites by orally administering to said ruminants a bolus, as described above, which continuously releases into the rumen of the treated animals, for a prolonged period of time, a therapeutically or prophylactically effective amount of the LL-F28249α, 23-(O-methyloxime)LL-F28249α or a derivative thereof.

Surprisingly, it is also found that control or prevention of nematode infestations in ruminants can be achieved with extremely low levels of LL-F28249α or 23-(O-methyloxime)LL-F28249α administered in a bolus of the invention comprising about 0.3% to less than 1.0% by weight of LL-F28249α, 23-(O-methyloxime)LL-F28249e or derivative thereof; about 144 to 164 by weight glycerol monostearate; about 3% to 5% by weight carnauba wax and about 78.01% to 82.7% by weight of barite.

Moreover, we have found that the boluses of the present invention are effective for providing prophylactic control of parasites that affect livestock and that such control is apparently derived from the continuous presence of exceedingly low levels of LL-F28249α or 23-(O-methyloxime)LL-F28249α. It is also observed that this prophylactic treatment of ruminants not only renders the animals free of infestation from nematodes, endoparasitic insects, ectoparasitic insects and acarids, but in addition provides significantly improved weight gains over untreated animals or animals treated with other anthelmintic, antibacterial or acaricidal agents.

DESCRIPTION OF THE PREFERRED EMBODIMENTS

Preferred bolus compositions effective for control and/or prevention of insect, nematode and acarid infestations of ruminants such as cattle, sheep, goats, bison, buffalo, deer and the like, comprise about 1.0 to 8.5% by weight of LL-F28249α or 23-(O-methyloxime)LL-F28249α, about 14.0% to 16.0% by weight of glycerol monostearate, about 3.0% to 5.0% by weight of carnauba wax and about 70.0% to 80.5% of barite.

One preferred embodiment of the present invention is a sustained release bolus for oral administration to ruminant animals, effective for protecting said animals for a prolonged period (up to about 6 months) against adult and larval infestation by helminths, endoparasitic insects ectoparasitic insects and acarids, consisting essentially of about 0.3% to 10% by weight of LL-F28249α, 23-(O-methyloxime-LL-F28249α or derivative thereof; about 10% to 20% by weight of glycerol monostearate about 3.0% to 10% by weight of carnauba wax and about 70.0% to 85% by weight of barium sulfate or barite fines. One especially preferred sustained release bolus consists essentially of about 0.3% to less than 1% by weight of LL-F28249α or 23-(o-methyloxime)LL-F28249α, about 14% to 16% by weight of glycerol monostearate, about 3.0% to 5.0% by weight of carnauba wax and about 78.01% to 82.7% by weight of barium sulfate or barite fines.

Surprisingly the prophylactic treatment of ruminants (exceedingly low dosage per day in some embodiments) not only prevents and/or controls nematodes, endo- and ectoparasitic insects and acarids, but also provides significantly improved weight gains over untreated animals or animals treated with other anthelmintic, antibacterial or acaricidal agents.

The preparation of sustained release bolus formulations of this invention is accomplished by blending on a weight basis, at a temperature below the melting point of the wax or mixture, about 0.3% to 10% active ingredient; about 3.0% to 10% carnauba wax; about 10% to 20% of glycerol monostearate and about 70% to 85% of a high-density, pharmacologically and pharmaceutically acceptable filler selected from barium sulfate and barite. The blend may be used in the injection molding step as is, or the blend may be pelletized or flaked using an extruder or flaker and the resulting pellets or flakes used for injection molding.

After blending, the mixture is discharged and either transferred to a pelletizing extruder or directly charged into the injection molder. If pelletizing is desired for improved homogeneity, the mixture may be pelletized utilizing a three-stage temperature profile comprising a feed section maintained at a temperature below the melting point of the wax, a hot transition section maintained at a temperature above the melting point of the wax and stearate, and a metering section maintained at a temperature below the melting point of the wax and stearate employing with a straight-through die equipped with a breaker plate, the die equipped breaker plate assembly being maintained at a temperature range which is similar to the range of the metering section.

The resulting extruded material is air cooled and cut into pellets of the desired size. Improved homogeneity may also be obtained by flaking the blend of active ingredient, wax, and barium sulfate or barite filler, and then prilling or wax granulating with commercially available equipment to produce better homogeneity.

The resulting pellets and/or dry blend materials are transferred to an injection molding system which is operated with a three stage temperature profile similar to that employed for pelletization; i.e, a feed phase below the mixture softening point, a transition phase above the softening point, and an injection phase wherein the mixture is injected into a mold at a temperature below the softening point of the. blend. The mold is cooled to solidify the bolus. Boluses produced are then removed from the mold and packaged.

While the above process may be carried out with barium sulfates or other fillers and weighting agents, barite fines are preferred. The use of barite fines in the process has several advantages over the use of purified USP grade barium sulfate, for example the use of barite increases the hardness of the bolus, and reduces the erosion rate of the bolus. Thus, the bolus provides a more controlled erosion rate and more sustained release rate of the LL-F28249α or the 23-(O-methyloxime)LL-F28249α.

Also, during the processing of the mixtures containing the wax, glycerol monostearate and active ingredient, it is found that the use of barite fines rather than USP grade barium sulfate produces less tacky and more easily handled solid mixtures.

Preparation of the boluses of this invention by injection molding avoids the need for cryogenic grinding of the solid mixture or the use of additional lubricants frequently required in other methods, such as tablet pressing of solids. Another advantage is that recycling of particles retained on the 100 mesh screens is avoided. Tablet pressing requires 100 mesh material for pressing since use of a >100 mesh material results in faster release of active agents from the bolus.

In a preferred method for the preparation of the LL-F28249α and 23-(O-methyloxime)LL-F28249α boluses of this invention by injection molding the cycle time is reduced to about 40 to 50 seconds. Full potency can be expected when operating conditions are maintained below 140° C. Actual operating conditions which appear to be highly desirable include: a) increasing temperature profile, i.e., an ambient barrel and a 90° C. nozzle temperature; b) injection time 20 sec.; c) injection pressure 0.5 tons psig and d) a cooling time of 20 sec. These conditions result in a melt temperature between 89° to 90° C., well below the critical temperature for decomposition. Time/temperature studies have indicated that continual recycle of sprues and runners is possible due to this excellent stability. The injection molded boluses have a higher density, are harder and seem to erode at a slower rate (as determined by methanol disintegration) than poured boluses. Also, theology data indicate that the better "wettability" of barite may protect the active ingredient from thermal decomposition.

While injection molding is a preferred method for preparation of boluses of this invention, it should be recognized that said boluses can be prepared by hand molding techniques. It should also be recognized that the size of the boluses can be significantly altered to provide bolus sizes for all sizes and species of ruminant animals. Using a hand molding technique, the monostearate and carnauba wax are blended, melted and heated to 105±5 deg. C. To this melt is added the active ingredient and blended to a uniform suspension. To this suspension is added the barite with continual mixing. Blending continues until a uniform creamy mixture is obtained. The resulting material is poured into a mold, allowed to cool to room temperature and demolded. The size and weight of the boluses prepared are, of course, determined by the dimensions of the molds employed.

The invention is further illustrated by the following non-limiting examples.

EXAMPLE 1

Inoculum Preparation

A typical medium used to grow the stages of inoculum is prepared according to ing formula:

| Dextrose | 1.0% |
|---|---|
| Dextrin | 2.0% |
| Yeast extract | 0.5% |
| NZ amine | 0.5% |
| Calcium carbonate | 0.1% |
| Water qs to | 100% |

This medium is sterilized. A 100 ml portion of this sterile medium, in a flask, is inoculated with mycelial scrapings from an agar slant of *Streptomyces cyaneogriseus noncyanogenus* NRRL 15773. The medium is then agitated vigorously on a rotary shaker for 48–72 hours at 28° C. providing primary inoculum. This primary inoculum is then used to inoculate one liter of the above sterile medium, which is then grown aerobically at 28° C. for 48 hours providing secondary inoculum.

EXAMPLE 2

Fermentation

A fermentation medium of the following formulation is prepared.

| Dextrin | 1.0% |
|---|---|
| Soya peptone | 1.0% |
| Molasses | 2.0% |
| Calcium carbonate | 0.1% |
| Water qs to | 100% |

This medium is sterilized and then a 30 liter portion is inoculated with one liter of secondary inoculum prepared as described in Example 1. The fermentation is conducted at 30° C., with a sterile air flow of 30 liters per minute, backpressure of 8 psig and agitation by an impeller operated at 500 rpm for 91 hours at which time the mash was harvested.

EXAMPLE 3

Isolation of LL-F28249α

A total of 26 liters of whole harvest mash, prepared as described in Example 2 is mixed with 1500 g of diatomaceous earth and filtered. The mycelial cake is washed with 5 liters of water and the filtrate and wash discarded. The mycelial cake is mixed with 10 liters of methanol for one hour, then filtered and washed with 5 liters of methanol. The methanol extract and methanol wash are combined and evaporated to an aqueous residue of about 1–2 liters. This aqueous residue is mixed with twice its volume of methylene chloride and mixed for ½ hour. The methylene chloride phase is separated and then concentrated to a syrup giving 27 g of crude material.

This 27 g of crude material is dissolved in a mixture of methylene chloride and methanol, filtered through cotton and anhydrous sodium sulfate and then evaporated, giving 7.0 g of an oil.

A 170 g portion of silica gel is slurried in 12.5% ethyl acetate in methylene chloride and poured to form a column 2.5×58 cm. The oil is dissolved in 12.5% ethyl acetate in methylene chloride and applied to the column. The column is developed with the same solvent mixture. The mobile phase is run at 1.3 ml/minute initially and 15 minute fractions are collected. The flow rate slowed to about 0.5 ml/minute after 10 fractions, so fractions 1–10 are 20 ml decreasing to about 10 ml uniformly and fractions 11–98 were about 7 ml. At fraction 99 the flow rate is increased to give 25 ml fractions in 10 minutes. A total of 105 fractions are collected. These fractions were tested by thin layer chromatography in ethyl acetate:methylene chloride (1:1).

Fractions 55–62 are combined and evaporated giving 150 mg of solid containing LL-F28249α and β.

The 150 mg of solid containing LL-F28249α and β are chromatographed by preparative HPLC using a reverse-phase column (Whatman C8, 2.2×50 cm) developed with 80% (v/v) methanol in water. The flow rate is about 10 ml/minute and 2 minute fractions are collected.

Fractions 58–69 are combined, the methanol is evaporated, t-butanol is added and the mixture is lyophilized, giving 60 mg of pure LL-F28249α.

This compound may be illustrated as follows:

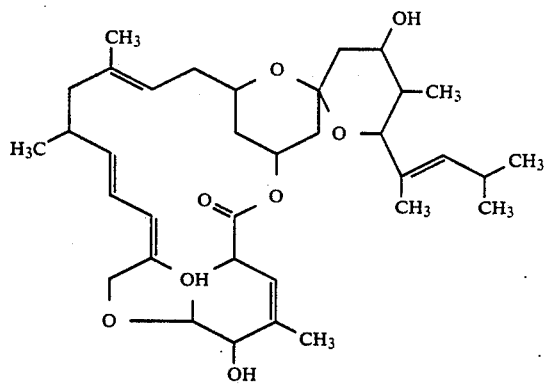

EXAMPLE 4

5-O-t-Butyldimethylsilyl-LL-F28249α

In 500 Ml of $CH_2Cl_2$, 70 g of LL-F28249α is stirred with 82.04 g of imidazole at 20° C. under $N_2$ atmosphere. Then, 43 g of t-butyldimethylsilyl chloride in 400 mL of $CH_2Cl_2$ is added over 5 minutes. After an hour, the reaction is assayed for completion by high performance liquid chromatography (HPLC), using $CH_3CN$/50% $H_2O$ in a curved gradient mode over 10 minutes on a Whatman Partisil CCS/$C_8$ rapid analysis column at 1 mL/min flowrate. Another 3 g of t-butyldimethylsilyl chloride is added, and after 3 hours the composition is 92.3% product, 0.3% LL-F28249α and 1.16% disilylated material. The mixture is diluted with $CH_2Cl_2$ and poured into 2 L of $H_2O$. The $CH_2Cl_2$ layer is separated. The aqueous portion is extracted with 2 L of $CH_2Cl_2$, and the combined organic layers are dried ($Na_2SO_4$). The $CH_2Cl_2$ is evaporated in vacuo to afford 166 g of the title compound that is identified by mass spectrometry and nuclear magnetic resonance (NMR) spectrometry.

EXAMPLE 5

5-O-t-Butyldimethylsilyl-23-oxo-LL-F28249α

In 5 L of dry CH$_2$Cl$_2$, 116 g of 5-O-t-butyl-dimethylsilyl LL-F28249α is stirred under N$_2$, and 540 g of NaOAc is added at 22° C., followed by addition of 172.5 g of pyridinium chlorochromate (PCC). After 1 hour, an additional 15 g of PCC is added since the reaction is incomplete by HPLC analysis. After 2 hours, another 10 g of PCC is added, and the reaction is stirred for a total of 5 hours. The mixture is poured into 6 L of ice-water mixture, and the CH$_2$Cl$_2$ is separated. The aqueous layer is extracted with CH$_2$Cl$_2$, and the combined CH$_2$Cl$_2$ layers are washed with water and dried (Na$_2$SO$_4$). The CH$_2$Cl$_2$ is evaporated in vacuo to afford 197.8 g of crude product, which is dissolved in 2 L of Et$_2$O and filtered. The Et$_2$O solution is washed with water (2×1000 mL), dried (Na$_2$SO$_4$) and evaporated to dryness to give 60 g of the title compound which is identified by mass spectrometry and NMR spectroscopy.

The pyridinium chlorochromate substituted with pyridinium dichromate in the above procedure also affords the title compound.

EXAMPLE 6

23-OXO-LL-F28249α

In 1.5 L of MeOH, 60 g of 5-O-t-butyldi-methylsilyl-23-oxo-LL-F28249α is dissolved by warming, and at 0° C., 30 g of p-toluenesulfonic acid in 300 mL of MeOH is added. The mixture is stirred for 3 hours and poured into 6 L of saturated NaHCO$_3$ solution in 6 L of H$_2$O. After stirring, the mixture is extracted with 4 L of EtOAc, and the layers are separate. The aqueous layer is saturated with NaCl and extracted with 2×6 L of EtOAc. The first EtOAc layer is washed with saturated NaCl solution, combined with the other EtOAc extracts and dried (Na$_2$SO$_4$). The EtOAc is evaporated in vacuo to afford 148.1 g of dark residue. The crude material is then chromatographed by HPLC on 1200 g of SiO$_2$ using 1% isopropanol in CH$_2$Cl$_2$ to elute and monitored by an ultraviolet detector/254 nM filter. Fractions 39–42 are combined and evaporated to dryness to afford 12.65 g of the title compound which analyzes as follows:

Anal. Calcd for C$_{36}$H$_{50}$O$_8$: C, 70.79; H, 8.25.
Found: C, 70.33; H, 8.31.
The title compound is further identified by mass spectrometry and NMR spectroscopy.

EXAMPLE 7

23-O-Methyloxime-LL-F28249α

In 930 mL of dry dioxane at room temperature, 70 g of 23-oxo-LL-F28249α, 11.8 g of NaOAc, 11.8 g of CH$_3$ONH$_2$·HCl and 2.1 mL of HOAc are added. The mixture is stirred under N$_2$ for 3 days, and after no starting material is detected by HPLC, 650 mL of dioxane is evaporated in vacuo. The residue is poured into 5 L of H$_2$O, and the product is extracted with CH$_2$Cl$_2$ (4×2 L). The combined extracts are washed with H$_2$O, dried (Na$_2$SO$_4$) and evaporated to dryness. The residue is dissolved in 1500 mL of Et$_2$O, and the solution is washed with H$_2$O, dried (Na$_2$SO$_4$) and evaporated to dryness. This gives 11.84 g of the title compound, which is identified by mass spectrometry and NMR spectroscopy. It also analyzes as follows:

Anal. Calcd for C$_{37}$H$_{53}$O$_8$N·1.5 H$_2$O: C, 66.64; H, 8.46; N, 2.10.
Found: C, 66.82; H, 8.13; N, 2.32.
This compound may be illustrated as follows:

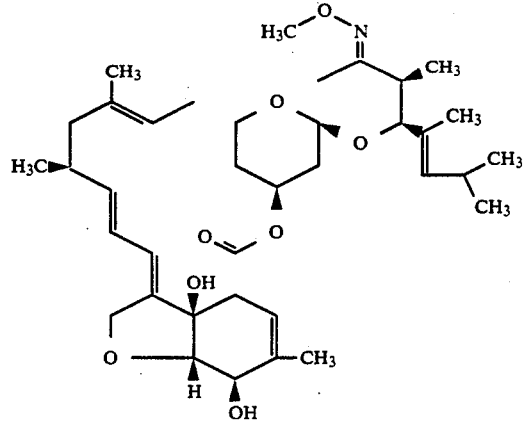

EXAMPLE 8

Preparation of Sustained Release Bolus

Boluses are made according to the following formulation:

| Ingredient | % |
| --- | --- |
| 23-(O-methyloxime)LL-F28249α (89% real) | 0.34 |
| Glycerol Monostearate | 15.95 |
| Carnauba Wax | 3.96 |
| Barite | 79.75 |

The monostearate and carnauba wax are blended, melted and heated to 105±5 deg. C. To this melt is added the active ingredient and blended to a uniform suspension. To this suspension is added the barite with continual mixing. Blending continues until a uniform creamy mixture is obtained. The resulting material is poured into a mold, allowed to cool to room temperature and demolded. The resulting boluses weigh between 51 and 53 grams. Each bolus is domed at both ends and ¾ in. thick by 7/8 in. wide by 3.0 in. long.

Specifications for glyceral monostearate indicate that this material should be a white powder or beads essentially free of foreign matter. The particle size should not exceed 5% on a U. S. Standard Sieve No. 20 and have an acid value of 2–3.0 and a moisture content of not more than 1.5%. Total monoglycerides should exceed 40%, but free acid should not exceed 1.5%.

Carnauba wax should be a yellow powder essentially free of foreign matter. 100% of the wax should pass through a U.S. Standard Sieve No. 80. The acid number of the wax should be 2.0–6.0 and acetone soluble resinous matter at 15° C. should not exceed 5.0%.

The barite should be a gray powder essentially free of foreign matter and having a bulk density of about 150 pounds per cubic foot. The particle size should be such that not more than 4% is retained on a No. 200 U.S. Standard Sieve and not less than 80% pass through a No. 325 U.S. Standard Sieve. The chemical analysis for the-acceptable product is BaSO$_4$ 90–94%; SiO$_2$ 7–8% and Fe$_2$O$_3$ 0.1–0.2%. The density of the boluses of this invention should be between about 2.35 and 2.6±0.6.

Other bolus compositions are prepared in the same manner and are reported in Table I below.

TABLE I

Slow Release Bolus Compositions

| Ingredient | A | B | C | D | E | F | G | H |
|---|---|---|---|---|---|---|---|---|
| 23-(O-methyloxime) LL-F28249 (89% real) | 0.34 | 1.69 | 8.44 | 1.70 | | | | |
| 23-(O-methyloxime) LL-F28249 (90% real) | | | | | 1.63 | 3.26 | 4.90 | 6.50 |
| Glycerol monostearate | 15.95 | 15.73 | 14.65 | 15.70 | 14.40 | 14.40 | 14.40 | 14.40 |
| Carnauba wax | 3.96 | 3.93 | 3.66 | 3.90 | 3.60 | 3.60 | 3.60 | 3.60 |
| Barite | 79.75 | 78.65 | 73.25 | 78.70 | 80.37 | 78.74 | 77.10 | 75.50 |
| | 100.0 | 100.0 | 100.0 | 100.0 | 100.0 | 100.0 | 100.0 | 100.0 |

EXAMPLE 9

Determination of Erosion rates of Boluses of the present invention

The drug release rates for boluses designated A, B and C in Table I are determined by initially assaying said boluses, for the compound 23-(O-Methyloxime)LL-28249α, which are to be administered to the calves selected for the test. These assays show that boluses which are to be evaluated contain 0, 71.3, 1035 or 1260 mg of 23-(O-Methyloxime)LL-28249α. The 50–53 gram boluses are broken in half, weighed and orally administered, one ½ bolus to each calf. The treated calves are then penned and fed and watered according to conventional or standard cattle raising procedures. The diet for all animals is a standard cattle ration.

At intervals of 70, 119 and 167 days after administration, four animals from each treatment group are necroposied and the boluses retreived and examined to determine whether the surface is rough or smooth and then weighed. The results are thereafter recorded and evaluated. This procedure is repeated at 119 days after treatment for a second group of animals from each treatment and then repeated again at 167 days with a third group of animals from each treatment group.

For convenience, the results obtained from each treatment group, four calves per group, are averaged and reported in Table II.

monostearate, carnauba wax and barite are prepared by blending the appropriate amounts of each ingredient in a blender maintained at about 80° C. for 10 minutes.

After blending, the mixture is discharged and transferred to a pelletizing extruder and/or directly charged to the injection molder.

If pelletizing is carried out, this mixture is then pelletized using a bell shaped temperature profile that has a cooled feed section (50°–60° C.), hot transition section (100°–110° C.) and a cooled metering section (5°–60° C.) with a straight-through 1/8 inch die equipped with a 20 mesh screen breaker plate. The die temperature is maintained at 55°–60° C. Resulting extruded rope is air cooled (air stream blowing at the die opening) and cut using a hot face cutter to ¼" inch long pellets.

In the case of direct feeding of the dry blend, a feeding system such as a Vibra-Screen may be used, to transfer the material to an injection molding system utilizing a hot runner system and a shut-off nozzle. Operating conditions for the injection molder should be the bell shaped temperature profile described for the pelleting operation above, e.g. fill time (10–20 sec.), injection time (10–20 sec.), injection pressure 0.5 tons psig, and hold time (5–10 sec.) yielding boluses weighing about 51 grams each and having a density of about 2.5 g/cc and a hardness as measured on a Delamar Press of about 77 to 80 kg.

Boluses prepared by this method are shown below.

| Bolus Compositions Prepared By Injection Molding | | | | |
|---|---|---|---|---|
| Ingredient | Bolus I | J | K | L |

TABLE II

Erosion Rate of Boluses A, B and C from Table I

| Average Bolus Assay 23-(O-methyloxime) LL-F28249alpha (mg) | Average Initial Bolus weight (mg) | Day Bolus Recovered | Average mg/hd/day delivery of 23-(O-methyloxime) LL-F28249alpha (mg) | Average animal weight for the period (kg) | Release rate mg/kg/day of 23-(O-methyloxime) LL-F28249alpha delivered from day 1 until recovery of Bolus | Average release rate mg/kg/day of 23-(O-methyloxime) LL-F28249alpha delivered between days 70 to 119 and 119 to 167 |
|---|---|---|---|---|---|---|
| 713 | 26.7 | 70 | 6.07 | 113.4 | 0.054 | — |
| 713 | 26.7 | 119 | 4.95 | 119.6 | 0.041 | 0.028 |
| 713 | 27.1 | 167 | 3.45 | 122.4 | 0.028 | 0.0014 |
| 1035 | 26.2 | 70 | 8.59 | 121.8 | 0.071 | — |
| 1035 | 26.7 | 119 | 6.19 | 111.0 | 0.056 | 0.025 |
| 1035 | 26.1 | 167 | 5.31 | 129.7 | 0.041 | 0.003 |
| 1260 | 25.8 | 70 | 10.41 | 129.0 | 0.081 | — |
| 1260 | 25.6 | 119 | 6.67 | 113.3 | 0.059 | 0.012 |
| 1260 | 25.8 | 167 | 7.09 | 129.2 | 0.055 | 0.06 |

EXAMPLE 10

Preparation of a Sustained Release Bolus Formulation and Evaluation Thereof for Control of Gastrointestinal Helminths and Boophilus Microplus Ticks on Cattle Sustained release bolus formulations consisting essentially of 23-(O-methyloxime)LL-F28249α, glycerol

| | % by weight | | | |
|---|---|---|---|---|
| 23-(O-methyloxime) LL-F28249α | 0.0 | 3.24 | 4.84 | 6.46 |
| Glycerol monostearate | 14.40 | 14.40 | 14.40 | 14.40 |
| Carnauba wax | 3.60 | 3.60 | 3.60 | 3.60 |
| Barite | 82.00 | 78.76 | 77.16 | 75.54 |
| | (weight in grams) | | | |

-continued

| Bolus Compositions Prepared By Injection Molding | | | | |
|---|---|---|---|---|
| Ingredient | Bolus I | J | K | L |
| 23-(O-methyloxime) LL-F28249α | 0 | 28.49 | 42.15 | 26.49 |
| Glycerol monostearate | 125.28 | 125.28 | 125.28 | 59.04 |
| Carnauba wax | 31.32 | 31.32 | 31.32 | 14.76 |
| Barite | 713.60 | 685.21 | 671.29 | 309.71 |

In order to evaluate the above-identified compositions for the control of gastrointestinal helminths and cattle tick infestations in or on cattle, the following tests are conducted.

Fifty-two abedeen angus calves, (less than one year of age) and on pasture, are selected for evaluation of the boluses described above and designated I, J, K and L.

The boluses contain 0, 713, 1035 or 1260 mg of 23-(O-methyloxime)LL-F28249α, respectively, per ½ bolus each of which weighs about 25 grams.

During the week before treatment two separate differential nematode egg counts are done on the calves and the severity of tick infestations assessed. The animals are ear tagged, weighed and assigned to one of four treatment groups, 12 calves per group. A fifth group of 4 animals is also ear tagged and weighed. This group is used to study the leasability of reintroducing boluses recovered after necropsy into other animals.

Differential nematode egg counts are done one week, two weeks, 1 month and monthly for 5 months or until there is no longer adequate control.

Data obtained are reported in Tables III and IV below where it can be seen that control animals, untreated for the first 67 days of the trial, remain severely infested throughout this portion of trial period. These animals are then treated with levamisole and the nematode infestations are very markedly reduced. Animals receiving the boluses of this invention containing from 713 mg to 1260 mg of 23-(O-methyloxime)-LL-F28249α are essentially free of nematode infestation from 28 days post treatment through 167 days post treatment.

Ticks are eliminated within one Week of treatment with the boluses containing 1035 mg of 1260 mg of 23-(O-methyloxime)LL-F28249α. Animals receiving boluses containing 713 mg of the active ingredient take two weeks to be cleared of ticks. The control animals have to be dipped in a tickicide solution to prevent mortality. The treated animals remain free of ticks for 97 days and until the cold weather sets in which eliminated tick infestations on control animals.

TABLE III

| | Evaluation of Boluses containing 23-(o-methyloxime) LL-F28249alpha for prolonged control of nematode infestations of cattle | | | | | | | |
|---|---|---|---|---|---|---|---|---|
| Days | 0 mg Bolus | | 713 mg Bolus | | 1035 mg Bolus | | 1260 mg Bolus | |
| Post-Treatment | Animals WB/Tl | Ave. EPG | Animals WB/Tl | Ave. EPG | Animals WB/Tl | Ave. EPG | Animals WB/Tl | Ave. EPG |
| 0 | 12/12 | 519 | 12/12 | 873 | 12/12 | 552 | 12/12 | 581 |
| 28 | 11/11 | 1041 | 12/12 | 0 | 12/12 | 0 | 12/12 | 0 |
| 44 | 11/11 | 1465 | 12/12 | 0 | 12/12 | 0 | 10/10 | 0 |
| 65 | 10/10# | 2043 | 12/12 | 0 | 12/12 | 0 | 10/10 | 0 |
| 97 | 7/7 | 108 | 8/8 | 0 | 8/8 | 0 | 6/6 | 0 |
| 116 | 7/7 | 308 | 7/8 | 25 | 8/8 | 0 | 6/6 | 0 |
| 140 | 3/3 | 317 | 4/4 | 25 | 5/5 | 0 | 3/3 | 0 |
| 167 | 2/3 | 717 | 4/4 | 0 | 3/5 | 0 | 1/3 | 100 |

WB/Tl = with boluses/total animals
Control animals treated with levamisole (3.75 mg/kg) on day 67 of the trial
EPG = Nematode eggs per gram of feces

TABLE IV

| | | | Evaluation of Boluses containing 23-(O-methyloxime) LL-F28249alpha for prolonged control of nematode populations in cattle | | | |
|---|---|---|---|---|---|---|
| NECROPSY DAY POST TREATMENT | BOLUS CONC. MG* | NO. ANIMALS WBOLUS/ TOTAL | PER CENT REDUCTION OF | | | |
| | | | HAEMONCHUS PLACEI | | OSTERTAGIA OSTERTAGI | |
| | | | ADULT | LARVAE | ADULT | LARVAE |
| 70 | 1260 | 4/4 | 100 | 100 | 100 | |
| | 1035 | 4/4 | 100 | 100 | 100 | |
| | 713 | 4/4 | 100 | 100 | 100 | |
| | 0** | 4/4 | 4617 (4000–6167) | 542 (333–667) | 200 (66–533) | |
| 119 | 1260 | 3/3 | 100 | 100 | 100 | 100 |
| | 1035 | 3/3 | 100 | 100 | 100 | 100 |
| | 713 | 3/4 | 100 | 100 | 100 | 100 |
| | 0** | 3/3 | 1752 (500–2400) | 674 (67–1155) | 441 (67–756) | 74 (0–133) |
| 167 | 1260 | 1/3+ | 98.5 | 97.3 | 92.8 | |
| | 1035 | 3/5 | 99.3 | 100 | 100 | |
| | 713 | 4/4 | 100 | 100 | 100 | |
| | 0** | 2/3 | 2067 (1467–2533) | 617 (533–1881) | 10130 (3200–22898) | |
| NECROPSY DAY POST TREATMENT | | | PER CENT REDUCTION OF | | | |
| | | | COOPERIA PUNCTATA | | OESOPHAGOSTOMUM | DICTYOCAULUS |
| | | | ADULT | LARVAE | ADULT | ADULT |
| 70 | | | 100 | — | 100 | 100 |
| | | | 99.9 | — | 100 | 100 |
| | | | 100 | — | 100 | 100 |
| | | | 35783 | 0 | 665 | 67 |

TABLE IV-continued

Evaluation of Boluses containing 23-(O-methyloxime) LL-F28249alpha for prolonged control of nematode populations in cattle

| | | | | |
|---|---|---|---|---|
| | (19600–51033) | | (310–1072) | (5–118) |
| 119 | 100 | 100 | 100 | 100 |
| | 100 | 100 | 100 | 100 |
| | 98.8 | 97.2 | 100 | 100 |
| | 23959 | 1322 | 228 | 120 |
| | (18778–32500) | (433–2533) | (60–400) | (0–319) |
| 167 | 73.4 | 100 | 100 | 100 |
| | 99.4 | 100 | 100 | 100 |
| | 99.5 | 100 | 100 | 100 |
| | 29567 | 400 | 413 | 2 |
| | (14033–59667) | (33–933) | (88–880) | (0–5) |

*Per head (In a half bolus [25+ grams])
**Number of nematodes: Numbers in ( )'s give the range
+Animal with bolus had no worms

EXAMPLE 11

Evaluation of Slow Release Boluses for Propylactic Control of Psoroptic Mange on Cattle Boluses containing 375 mg of 23-(O-methyloxime)LL-F28249α per ½ bolus, are prepared by the injection molding technique described in Example 10. The boluses prepared have the following composition.

| Ingredient | % by weight | Grams |
|---|---|---|
| 23-(O-methyloxime) LL-F28249α | 1.53 | 1.61 |
| Glycerol monostearate | 15.73 | 16.52 |
| Carnauba wax | 3.93 | 4.12 |
| Barite | 78.81 | 82.75 |
| | 100.00 | 105.00 |

Cattle receiving the boluses are given one half of a 50 gram bolus containing 750 mg of 23-(O-methyloxime)LL-F28249α.

Mixed heifers are selected for the trial. The animals are placed in a dry lot and started on a health program to protect against common disease problems. They are ear tagged and placed in stanchions to prevent licking the mange infestation.

Live mites are then transferred to each animal. The transfers are made by taking scrapings from heavily infested donor animals and transferring them to candidate animals.

Four uninfested animals are randomly selected from animals which have not been placed in the barn. These four animals later receive the bolus treatment and are infested one week later. Mites are placed on each of these animals, six times during the next two weeks.

Care is taken to prevent cross contamination between animals. Scraping are made at weekly intervals and evaluated the same day.

The mites are counted by stage, using a 20–30 x dissecting microscope. The 375 mg bolus prevented the Psoroptic mange infestation from establishing on the cattle receiving six heavy challenges of mites.

Data obtained are reported in Table V below.

TABLE V

Average number of live mites (*Psoroptes ovis*) per animal

| Treatment | 1 day prior to Treatment | 8 | 16 | 22 | 29 | 34 | 43 | 47 | 56 |
|---|---|---|---|---|---|---|---|---|---|
| Bolus containing | XX | — | — | 0 | 0 | 0 | 0 | 0 | 0 |
| 375 mg 23-(O-methyloxime) | XX | — | — | 0 | 0 | 0 | 0 | 0 | 0 |
| LL-F28249alpha | XX | — | — | 0 | 0 | 0 | 0 | 0 | 0 |
| | XX | — | — | 0 | 0 | 0 | 0 | 0 | 0 |
| Untreated Control | 274 | 130 | 421 | 757 | 285 | 464 | deceased | | |
| | 123 | 149 | 50 | 403 | 218 | deceased | | | |
| | 69 | 66 | 39 | 20 | 6 | 27 | 14 | 16 | 14 |
| | 1 | 4 | 3 | 9 | 1 | 5 | 9 | 16 | 16 |

XX = Bolus group was not infested until 1 week after test initiated; and then it was found that mite colonies could not be established on bolus treated animals. Counts based on 2 scrapings/animal/sample period
— = mite colony could not be established

EXAMPLE 12

Evaluation of Boluses Containing 23-(O-Methyloxime) LL-F28249α for the Sucking Lice and Face Flies on Cattle The Boluses used in these evaluations are prepared by an injection molding technique as described in Example 10. The prepared boluses have the following compositions.

| | Bolus I | | Bolus II | | Bolus III | |
|---|---|---|---|---|---|---|
| Ingredient | % by wt. | grams | % by wt. | grams | % by wt. | grams |
| 23-(O-methyloxime LL-F28249α | 1.62 | 6.64 | 3.24 | 28.49 | 4.84 | 42.15 |
| Glycerol Monostearate | 14.40 | 59.04 | 14.40 | 125.28 | 14.40 | 125.28 |
| Carnauba wax | 3.60 | 14.76 | 3.60 | 31.32 | 3.60 | 31.32 |
| Barite | 80.38 | 329.56 | 78.76 | 685.21 | 77.16 | 671.29 |

For evaluation the boluses are broken in half.
Bolus I Contains 375 mg AI/half bolus
Bolus II Contains 750 mg AI/half bolus
Bolus III Contains 1125 mg AI/half bolus
AI = active ingredient Prior to treatment all animals are weighed, ear tagged, and inspected for lice. The number of lice are estimated from visual inspection of 2-3 cm hairparts from each of the following locations: ear, eyes, muzzle, jaw, brisket, dewlap, shoulder, backline, tailhead, and hips. Animals are randomly assigned to groups including 3 treatments and 1 control of 5 animals each. Groups I, II, and III are given boluses containing the experimental compound while group 1 is untreated. All animals are confined to 2 acre lots and given free access to alfalfa hay and mineral supplement. Lice on the animals are assessed at days 7, 14, 28, and bimonthly throughout the test.

Lice estimates are made while the animals are restrained in a head gate under artificial lighting.

Fecal samples (app. 10 g) are taken for nematode analysis on days 7, 28, and monthly thereafter. Samples are stored at $-10°$ C.

All bolused treatment groups (375 mg, 750 mg and 1125 mg) of animals have significantly reduced levels of the blue cattle louse, *Solenoptes capillatus* at 1 week post-treatment.

Complete control of sucking lice (*Solinoptes capillatus*) on all bolus treated cattle is achieved for 100 days.

EXAMPLE 13

Evaluation of a Slow Release Bolus for Controlling Hypoderma Spp. in Cattle for a Prolonged Period Boluses used in this evaluation are prepared by injection molding as described in Example 10 above. The boluses evaluated have the following composition:

| Ingredient | by wt. | grams |
|---|---|---|
| 3-(O-methyloxime) LL-F28249α | 1.6 | 3.2 |
| Glycerol monostearate | 14.4 | 28.8 |
| Carnauba wax | 3.6 | 7.2 |
| Barite | 80.4 | 160.8 |
| | 100.0 | 200.0 |

In these tests mixed breed cattle naturally infested with first instar Hypoderma spp. are randomly divided in treatment groups of 4 calves each. One group serves as untreated controls another group receives one half of a 50-54 gram bolus containing 375 mg of 23-(O-methyloxime)LL-F28249α. The half boluses are administered to the calves with a balling gun.

After administration efficacy is determined through visual examination and palpation of the backs of the calves, on a weekly basis, for presence of warbles. Treatment with the 23-(O-methyloxime)LL-F-28249α boluses are complete effective against Hypoderma spp. No grubs appear in the backs of cattle receiving the 375mg boluses containing the above-said compound over the 72 day trial; however, untreated control animals average 12 (range 4-19) grubs/head at the peak count at 58 days and 8.8 at 72 days.

EXAMPLE 14

Evaluation of Boluses Containing From 75 to 1875 Mg of LL-F28249α for Prolonged Control of Nematodes and Ticks on Cattle The boluses for evaluation are prepared as follows:

The monostearate and carnauba wax are blended, melted and heated to $105° \pm 5°$ C. To this melt is added the active ingredient and blended to a uniform suspension. To this suspension is added the barite with continual blending. Blending continues until a uniform creamy mixture is obtained. The resulting material is poured into a mold, allowed to cool to room temperature and demolded. The resulting boluses weigh between 51 and 53 grams. Each bolus is domed at both ends and ¾ in. thick by ⅞ in. wide by 3.0 in long.

One half boluses (weight 25.5 to 27.0 g) and are administered to cattle on pasture. Efficacy is monitored over 120 days by determining the number of internal and external parasites.

| Ingredient | % by wt | gms | % by wt | gms | % by wt | gms |
|---|---|---|---|---|---|---|
| LL-F28249α | 0.34 | 5.1 | 1.69 | 25.35 | 8.44 | 126.6 |
| Glycerol monostearate | 15.95 | 239.25 | 15.73 | 235.95 | 14.65 | 219.75 |
| Carnauba wax | 3.96 | 59.40 | 3.93 | 58.95 | 3.66 | 54.90 |
| Barite | 79.75 | 1196.25 | 78.65 | 1178.75 | 73.25 | 1098.75 |

Bolus I contains 75 mg LL-F28249α per half bolus, bolus II contains 375 mg LL-F28249α per half bolus and bolus III contains 1875 mg LL-F28249α per half bolus.

In this test pastured animals are randomly divided into groups of 5 animals per group and ear-tagged. The feces of all animals is examined prior to the tests in order to determine the average number of nematode eggs per gram of feces of the test animals. All calves appear to have between 2700 and 3000 eggs per gram of feces. The test is begun with all animals receiving one half of a bolus weighing about 25 to 27 grams. Control animals receive 3.75 mg/kg of body weight of levamisole at the start of the test and on day 62; other treatment groups receive half boluses I, II or III as described above containing 75, 375 or 1875 mg of LL-F28249α, respectively. The animals are then placed in individual paddocks and examined at intervals during the holding period up to 120 days. On day 7, 16, 32, 62, 91 and 106 following treatment, feces are collected from each animal and the average number of nematode eggs per gram of feces is determined. Data obtained show that the 75 mg bolus reduced the nematode egg counts and nematode burdens to levels below the two treatments with levamisole. The 375 mg and 1875 mg bolus gave 99.9% reduction of nematode eggs within one week and gave 99.9% control of nematodes. The superior weight performance of animals receiving the 375 and 1875 mg boluses were highly significant statistically. The weight of animals receiving the 75 mg bolus was equivalent to the levamisole control.

TABLE VI

Evaluation of boluses containing 75, 375 and 1875 mg of LL-F28249alpha for control of nematodes in cattle

| Treatment | # Calves | Days 0 | 7 | 62 | 119 |
|---|---|---|---|---|---|
| (Recommended dose) Levamisole day 0 and day 62 | 10 | (2850) | 5 (99.9%) | (Levamisole) 755 | 146 |
| Bolus I (75 mg) | 10 | (2850) | 940 (67%) | 205 | 5 |
| Bolus II (375 mg) | 10 | (2850) | 0 (100%) | 0 | 5* |
| Bolus III (1875 mg) | 10 | (2850) | 0 (100%) | 0 | 5** |

*1 Animal had 25 EPG
**6 Animals with bolus had 0 EPG's; 4 animals without bolus had positive EPG's

TABLE VII

EFFICACY OF ll-F28259 BOLUS AGAINST NEMATODES IN CATTLE
% CONTROL OF NEMATODES

| Treatment | # Cattle | Haemonchus | Ostertagia | Cooperia | Oesophlogostonum |
|---|---|---|---|---|---|
| 75 mg bolus | 10 | 92 | 100 | 0 | 25 |
| 375 mg bolus | 10 | 100 | 100 | 97 | 99+ |
| 1875 mg bolus | 10 | 100 | 100 | 99+ | 100 |
| Levamisole Control Avg. number worms (dewormed 57 days earlier) | 10 | 2325 | 729 | 5937 | 117 |

TABLE VIII

Weight gains of cattle receiving levamisole 3.75 mg/kg on day 0 and day 62 and from boluses containing LL-F28249alpha and delivering 0.37 mg/hd/day, 1.96 mg/hd/day or 3.76 mg/hd/day of LL-F28249alpha

| Treatment | Average weight gains (Kg) from Day 0 | | |
|---|---|---|---|
| | Days 7 | 62 | 110 |
| Levamisole (3.75 mg/kg on day 0 and day 62) | 7 | 0 | 21 |
| Bolus I 75 mg (0.0031 mg/kg/day) | 5 | 7 | 24 |
| Bolus II 375 mg (0.016 mg/kg/day) | 6 | 11 | 37 |
| Bolus III 1875 mg (0.031 mg/kg/day) | 8 | 15 | 40 |

What is claimed is:

1. A sustained release bolus for oral administration to ruminant animals, effective for protecting said ruminant animals against adult and larval infestation by helminths, endoparasitic insects, ectoparasitic insects and acarids, consisting of about 0.3% to 10% by weight of a compound selected form the group consisting of LL-F28249α or 23-(O-methyloxime)LL-F28249α; about 10% to 20% by weight of glycerol monostearate; about 3.0% to 10.0% by weight of carnauba wax and about 70.0% to 85% by weight of barium sulfate or barite fines, and wherein said bolus is capable of releasing into the digestive tract of sad ruminant animals about 0.001 to 0.075 mg per kg of body weight per day of said compound or a period of about 120 to 180 days.

2. The sustained release bolus according to claim 1 comprising about 1.0% to 8.5% by weight of said L-F28249α or 23-(o-methyloxime)LL-F28249α, about 14% to 16% by weight of glycerol monostearate, about 3.0% to 5.0% by weight of carnauba wax and about 70% to 80% by weight of barite.

3. A sustained release bolus according to claim 1 effective for the control or prevention of helminth infestations in ruminant animals comprising about 0.3% to 1.0% by weight of LL-F28249α or 23-(o-methyloxime)LL-F28249α, about 14% to 16% by weight of glycerol monostearate, about 3.0% to 5.0% by weight of carnauba wax and about 78.01% to 82.7% by weight of barium sulfate or barite fines.

4. The sustained release bolus according to claim 1 for the control of nematodes in cattle, wherein said bolus is capable of releasing into the digestive tract of said treated animal about 0.0031 mg per kg of animal body weight per day to 0.031 mg per kg of animal body weight per day of LL-F28249α or 23-(o-methyloxime)LL-F28249α.

5. The sustained release bolus according to claim 2 for the prevention or inhibition of nematode and tick infestations of cattle wherein the compound is present in the range of about 75 mg to 1875 mg.

6. The sustained release bolus according to claim 2 for the systemic control of ectoparasitic insect infestations of ruminant animals wherein said bolus further comprises from about 375 mg to 1875 mg of LL-F282249α or 23-(o-methyloxime)-LL-F28249α.

* * * * *

UNITED STATES PATENT AND TRADEMARK OFFICE
CERTIFICATE OF CORRECTION

PATENT NO. : 5,322,692

DATED : June 21, 1994

INVENTOR(S) : Irwin Boyden Wood, et al.

It is certified that error appears in the above-indentified patent and that said Letters Patent is hereby corrected as shown below:

Claim 1, column 17, line 56 should read:
"compound selected from the group consisting of LL-"

Claim 1, column 17, line 62 should read:
"the digestive tract of said ruminant animals about 0.001"

Claim 1, column 18, line 30 should read:
"pound for a period of about 120 to 180 days."

Claim 2, column 18, lines 34-34 should read:
"comprising about 1.0% to 8.5% by weight of said LL-F28249α, or 23-(o-methyloxime)LL-F28249α, about"

UNITED STATES PATENT AND TRADEMARK OFFICE
CERTIFICATE OF CORRECTION

PATENT NO. : 5,322,692
DATED : June 21, 1994
INVENTOR(S) : Irwin Boyden Wood, et al.

It is certified that error appears in the above-indentified patent and that said Letters Patent is hereby corrected as shown below:

Claim 6, column 18, lines 60-61 should read:
"comprises from about 375 mg to 1875 mg of LL-F28249α or 23-(o-methyloxime)-LL-F28249α."

Signed and Sealed this

Twenty-eighth Day of January, 1997

Attest:

BRUCE LEHMAN

Attesting Officer    Commissioner of Patents and Trademarks